Oct. 28, 1952 J. M. GARABEDIAN Plant Pat. 1,141

PEACH TREE

Filed Nov. 26, 1951

WITNESS

Addison J. Avery

INVENTOR

John M. Garabedian

Webster & Webster

ATTYS

Patented Oct. 28, 1952

Plant Pat. 1,141

UNITED STATES PATENT OFFICE 1,141

PEACH TREE

John M. Garabedian, Fresno, Calif.

Application November 26, 1951, Serial No. 258,237

1 Claim. (Cl. 47—62)

This invention relates in particular to a new and distinct variety of peach tree characterized by freestone fruit having a late ripening period, and of good flavor, size, texture, and color; all of these features being of advantage—commercially—in a late market peach for dessert use.

This new variety originated as a seedling of the Kirkman Gem shown in United States Plant Patent No. 506, but is best compared with the Kirkman peach shown in United States Plant Patent No. 920. As distinguished from this latter peach, the present variety bears fruit which is rounder in shape; shows more yellow ground color; and—most important—ripens approximately two weeks later.

A closely similar characteristic of the present variety of peach and the peach of United States Plant Patent No. 920 is that the fruit of both will remain on the trees for a considerable length of time without over-ripening, thus permitting of leisurely harvest.

The present variety was originated, and subsequently successfully asexually reproduced, in the following manner:

Seed of the Kirkman Gem peach was planted in my orchard plot near Madera, California, and—after careful and continuing observation of the resultant, open-pollenated seedings—the present variety was selected as being new and distinct. It was subsequently budded onto an older tree in the orchard, and the reproductions carry forward all of the novel characteristics of the parent. There are now a substantial number of asexual reproductions of the variety.

Figure 1:
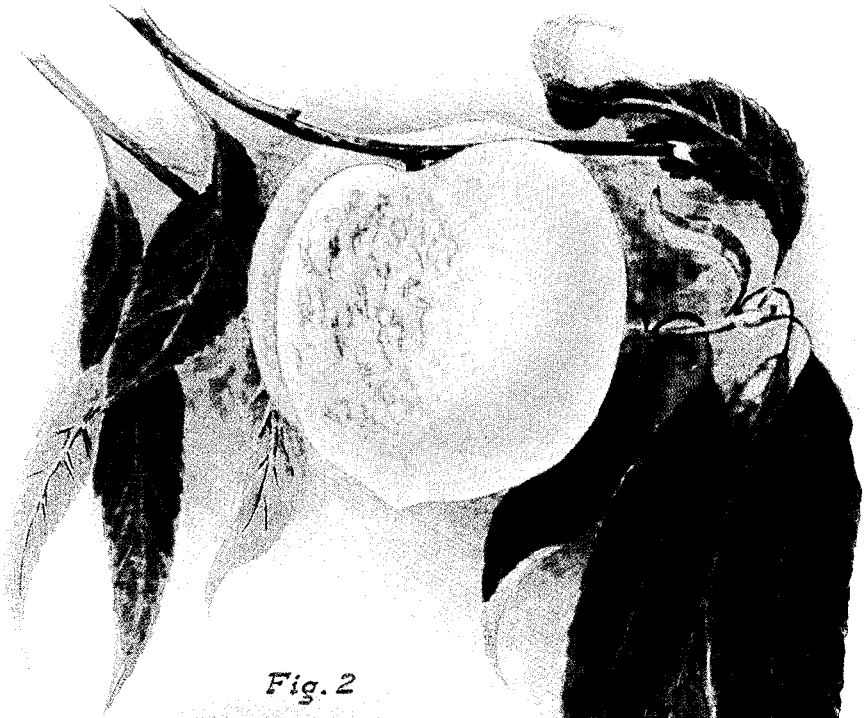
Fig. 1 is a perspective view of one of the fruit, together with twigs and leaves.
Figure 2:
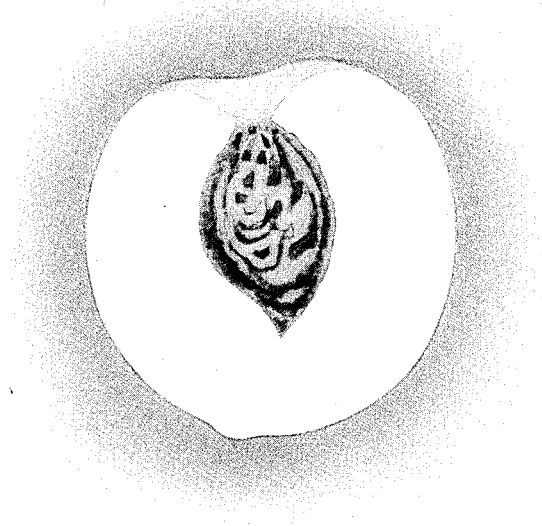
Fig. 2 is a sectional view of one of the fruits with the stone exposed.

Referring now more specifically to the pomological details of this new and distinct variety of peach tree, the following is an outline description thereof; all major color plate identifications being by reference to Maerz and Paul Dictionary of Color.

Tree: Large; medium vigorous; upright—spreading; open; vase form; productive.

Trunk: Medium size; medium texture.

Branches: Medium size; medium texture; reddish brown.

*Lenticels.*—Medium number; medium size.

Leaves: Medium—small. Average length, 6″ to 6¾″; average width, 1″ to 1¼″. Linear—lanceolate; acutely pointed; medium thick; smooth. Color—medium green (23–L–6) on top; lighter green (22–J–2) on under side.

*Margin.*—Serrate.

*Petiole.*—Medium length; medium thickness.

*Glands.*—Average number—three. Medium to small; reniform; green. Position—at base of the blade, only rarely one or two on petiole next to the blade base.

*Stipules.*—Lacking.

Flower buds: Medium to small size; medium length; obtuse—conic; appressed; pubescent.

Flowers: Dates of first and full bloom—approximately February 28th and March 8th, respectively. Early—blooms with the Quetta nectarine and five days ahead of the Kirkman Gem peach (United States Plant Patent No. 920).

*Size.*—Large.

*Color.*—Pink.

Fruit:

*Size.*—Uniform; medium. Average diameter axially, 2½″ to 3″; average transversely in suture plane, 3″ to 3¼″.

*Form.*—Uniform; symmetrical; globose to broadly ovate.

*Suture.*—An inconspicuous line; slight depression beyond pistil point.

*Ventral surface.*—Rounded or slightly lipped throughout one side; lips equal.

*Cavity.*—Flaring; abrupt. Average depth, ½″; average breadth, ¾″ to 1″.

*Base.*—Rounded.

*Pistil point.*—Apical.

Skin: Medium thickness; medium tender; tenacious to flesh.

*Tendency to crack.*—None

*Down.*—Moderate to scant; short; does not roll up when rubbed.

*Color.*—Yellow under color (11–K–6) with a red blush (5–K–10 to 6–L–9) mottled on the sunny side covering up to one-third of the fruit surface.

Flesh:

*Color.*—Yellow (9–L–5 to 9–L–8) streaked with red (3–L–4) next to stone.

*Surface of pit cavity.*—Red with yellow fibers.

*Amagdylin.*—Scant.

*Juice.*—Moderate.

*Texture.*—Firm; fine; meaty; melting.

*Fibers.*—Few; tender.

*Ripens.*—Evenly.

*Flavor.*—Mild.

*Aroma.*—Wanting.

*Eating quality.*—Good.

Stone: Free; parts from flesh smoothly.

*Size.*—Medium. Average length, 1⅜″ to 1½″; average breadth, 1″; average thickness, $\frac{11}{16}$″ to ¾″.

*Form.*—Oval.

*Base.*—Oblique.

*Hilum.*—Broad; oval.

*Apex.*—Rounded; acuminate.

*Sides.*—Equal.

*Surface.*—Irregularly furrowed near base; ridged toward apex; pitted from base to above center.

*Ridges.*—Rounded.

*Pits.*—Circular to elongated

*Ventral edge.*—Medium, without wing throughout.

*Dorsal edge.*—Narrow, with medium narrow groove throughout.

*Ridges.*—On either side—interrupted.

*Color.*—Brown (7–C–12 to 7–H–12).

Use: Market; dessert.

Keeping quality: Good.

Shipping quality: Good.

As compared to other varieties of peach trees the present variety—as aforesaid—more closely resembles the Kirkman peach which is the subject of United States Plant Patent No. 920; the prime distinguishing feature being that here the fruit has a date of first picking which falls approximately two weeks later. In the year 1951 the date of first picking of the present variety was the first few days of October, whereas the peach of United States Plant Patent No. 920 had its first picking in mid-September.

This late harvest season, coupled with the fact that the fruit is rounder in shape and shows more yellow ground color than the peach of United States Plant Patent No. 920 makes the present variety very desirable commercially, especially as a dessert peach; the large size and excellent texture and flavor of the flesh further contributing to the desirability of the fruit.

The tree and its fruit herein described may vary in slight detail due to climatic and soil conditions under which the variety may be grown.

Having thus described my invention, I claim:

A new and distinct variety of peach tree, substantially as described and illustrated, bearing yellow-fleshed freestone fruit which—as compared to the fruit of the peach tree of United States Plant Patent No. 920—ripens approximately two weeks later; is rounder in shape; and shows more yellow ground color.

JOHN M. GARABEDIAN.

No references cited.